(12) United States Patent
Straub et al.

(10) Patent No.: US 12,029,486 B2
(45) Date of Patent: Jul. 9, 2024

(54) LOW COST FUNDUS IMAGER WITH INTEGRATED PUPIL CAMERA FOR ALIGNMENT AID

(71) Applicants: Carl Zeiss Meditec, Inc., Dublin, CA (US); Carl Zeiss Meditec AG, Jena (DE)

(72) Inventors: Jochen Straub, Pleasanton, CA (US); Robert Sprowl, Livermore, CA (US); Yuan Liu, Dublin, CA (US); Matthew J. Everett, Livermore, CA (US)

(73) Assignees: CARL ZEISS MEDITEC, INC., Dublin, CA (US); CARL ZEISS MEDITEC AG, Jena (DE)

( * ) Notice: Subject to any disclaimer, the term of this patent is extended or adjusted under 35 U.S.C. 154(b) by 552 days.

(21) Appl. No.: 17/277,177

(22) PCT Filed: Sep. 24, 2019

(86) PCT No.: PCT/EP2019/075770
§ 371 (c)(1),
(2) Date: Mar. 17, 2021

(87) PCT Pub. No.: WO2020/064778
PCT Pub. Date: Apr. 2, 2020

(65) Prior Publication Data
US 2021/0369109 A1    Dec. 2, 2021

Related U.S. Application Data

(60) Provisional application No. 62/738,572, filed on Sep. 28, 2018.

(51) Int. Cl.
| A61B 3/12 | (2006.01) |
| A61B 3/00 | (2006.01) |
| A61B 3/15 | (2006.01) |

(52) U.S. Cl.
CPC .............. *A61B 3/12* (2013.01); *A61B 3/0008* (2013.01); *A61B 3/0033* (2013.01); *A61B 3/158* (2013.01)

(58) Field of Classification Search
CPC ....... A61B 3/12; A61B 3/0008; A61B 3/0033; A61B 3/158; A61B 3/10
(Continued)

(56) References Cited

U.S. PATENT DOCUMENTS

| 3,547,512 A | 12/1970 | Baer |
| 3,915,564 A | 10/1975 | Urban |

(Continued)

FOREIGN PATENT DOCUMENTS

| CN | 201920702 | 8/2011 |
| CN | 105662332 | 6/2016 |

(Continued)

OTHER PUBLICATIONS

Advisory Action received for U.S. Appl. No. 15/246,926, mailed on Mar. 12, 2019, 3 pages.
(Continued)

*Primary Examiner* — Mohammed A Hasan
(74) *Attorney, Agent, or Firm* — Snell & Wilmer L.L.P

(57) ABSTRACT

A low cost fundus camera uses LED light sources placed adjacent the camera's imaging stop, and thereby eliminates the need for optics for introducing the light source to the camera's optical path. Lens reflex in the pupil relay is avoided by using only reflective optics in the pupil relay. Reflex from the LED is mitigated by actuating each LED separately, one at a time, and capturing a separate image with each actuated LED. Reflex-free regions of each captured image are extracted and combined to create a composite reflex-free image.

21 Claims, 8 Drawing Sheets

(58) Field of Classification Search
USPC ....................................................... 351/206
See application file for complete search history.

(56) References Cited

U.S. PATENT DOCUMENTS

| | | | |
|---|---|---|---|
| 4,135,791 A | 1/1979 | Govignon | |
| 4,170,398 A | 10/1979 | Koester | |
| 4,400,070 A | 8/1983 | Isono et al. | |
| 4,478,482 A | 10/1984 | Koester | |
| 4,732,466 A | 3/1988 | Humphrey | |
| 4,768,874 A | 9/1988 | Webb et al. | |
| 4,838,679 A | 6/1989 | Bille | |
| 4,854,692 A | 8/1989 | Kobayashi | |
| 4,991,953 A | 2/1991 | Pflibsen et al. | |
| 5,028,802 A | 7/1991 | Webb et al. | |
| 5,177,511 A | 1/1993 | Feuerstein et al. | |
| 5,239,178 A | 8/1993 | Derndinger et al. | |
| 5,757,463 A | 5/1998 | Kohayakawa | |
| 5,784,148 A | 7/1998 | Heacock | |
| 5,861,939 A | 1/1999 | Heacock | |
| 5,984,474 A | 11/1999 | Schweitzer et al. | |
| 6,236,877 B1 | 5/2001 | Elsner et al. | |
| 6,267,477 B1 | 7/2001 | Karpol et al. | |
| 6,640,124 B2 | 10/2003 | Elsner et al. | |
| 7,284,859 B2 | 10/2007 | Ferguson | |
| 7,292,390 B2 | 11/2007 | Lin et al. | |
| 7,331,669 B2 | 2/2008 | Elsner | |
| 7,335,898 B2 | 2/2008 | Donders et al. | |
| 7,477,380 B2 | 1/2009 | Knebel et al. | |
| 7,567,726 B2 | 7/2009 | Westphal | |
| 7,586,086 B2 | 9/2009 | Lauer | |
| 7,648,242 B2 | 1/2010 | Ferguson et al. | |
| 7,659,971 B2 * | 2/2010 | Warden | A61B 3/1015 356/124 |
| 7,706,584 B2 | 4/2010 | Saggau et al. | |
| 7,768,652 B2 | 8/2010 | Everett | |
| 7,831,106 B2 | 11/2010 | Elsner et al. | |
| 7,854,510 B2 | 12/2010 | Verdooner et al. | |
| 8,100,531 B2 | 1/2012 | Liesfeld et al. | |
| 8,237,835 B1 | 8/2012 | Muller et al. | |
| 8,363,958 B2 | 1/2013 | Everett et al. | |
| 8,488,895 B2 | 7/2013 | Muller et al. | |
| 8,714,743 B2 | 5/2014 | Verdooner et al. | |
| 8,789,950 B2 | 7/2014 | Mensink et al. | |
| 8,814,362 B2 | 8/2014 | Verdooner et al. | |
| 11,672,421 B2 * | 6/2023 | Tumlinson | A61B 3/152 351/208 |
| 2004/0207811 A1 | 10/2004 | Elsner | |
| 2005/0012899 A1 | 1/2005 | Ferguson et al. | |
| 2005/0105044 A1 * | 5/2005 | Warden | G01M 11/0235 351/159.08 |
| 2005/0254008 A1 | 11/2005 | Ferguson et al. | |
| 2006/0177205 A1 * | 8/2006 | Steinkamp | A61B 3/14 396/18 |
| 2006/0228011 A1 | 10/2006 | Everett et al. | |
| 2007/0031002 A1 | 2/2007 | Venkatesh et al. | |
| 2007/0291277 A1 | 12/2007 | Everett et al. | |
| 2009/0244482 A1 | 10/2009 | Elsner et al. | |
| 2010/0128221 A1 | 5/2010 | Muller et al. | |
| 2011/0234977 A1 | 9/2011 | Verdooner | |
| 2012/0212598 A1 | 8/2012 | Mowrey et al. | |
| 2012/0249956 A1 | 10/2012 | Narasimha-Iyer et al. | |
| 2013/0222763 A1 | 8/2013 | Bublitz et al. | |
| 2014/0232987 A1 | 8/2014 | Westphal et al. | |
| 2016/0100754 A1 | 4/2016 | Dobashi | |
| 2017/0049323 A1 | 2/2017 | Bublitz et al. | |
| 2018/0014727 A1 * | 1/2018 | Bublitz | A61B 3/14 |

FOREIGN PATENT DOCUMENTS

| | | | |
|---|---|---|---|
| DE | 102011053880 A1 | 3/2013 | |
| DE | 102011114753 A1 | 4/2013 | |
| EP | 2338407 A1 | 6/2011 | |
| JP | 67301 A | 1/1994 | |
| JP | 2003079579 | 3/2003 | |
| JP | 2016077337 | 5/2016 | |
| JP | 2018002249 | 1/2018 | |
| JP | 2018504219 | 2/2018 | |
| JP | 2019118720 | 7/2019 | |
| WO | WO-2012059236 A1 | 5/2012 | |

OTHER PUBLICATIONS

Final Office Action received for U.S. Appl. No. 15/246,926, mailed on Nov. 16, 2018, 5 pages.
International Search Report and Written Opinion received for PCT Patent Application No. PCT/EP2014/055076 mailed on Oct. 13, 2014, 22 pages.
International Search Report and Written Opinion received for PCT Patent Application No. PCT/EP2019/075770 mailed on May 6, 2020, 17 pages.
Invitation to Pay Additional Fees received for PCT Patent Application No. PCT/EP2014/055076, mailed on Jul. 25, 2014, 8 pages.
Non-Final Office Action received for U.S. Appl. No. 15/246,926, mailed on Nov. 30, 2017, 4 pages.
Notice of Allowance received for U.S. Appl. No. 14/207,229, mailed on May 20, 2016, 7 pages.
Notice of Allowance received for U.S. Appl. No. 15/246,926, mailed on Jun. 4, 2019, 7 pages.
Petráň et al., (1968). "Tandem-Scanning Reflected-Light Microscope," Journal of the Optical Society of America, 58(5):661-664.
Poher et al., (2008). "Improved Sectioning in a Slit Scanning Confocal Microscope," Optics Letters, 33(16):1813-1815.
CNIPA, First Office Action and Search Report dated Sep. 29, 2023 in CN Serial No. 201980063270.8.

* cited by examiner

LOW COST FUNDUS IMAGER WITH INTEGRATED PUPIL CAMERA FOR ALIGNMENT AID

PRIORITY

This application is a National Phase application under 35 U.S.C. § 371 of International Application No. PCT/EP2019/075770, filed Sep. 24, 2019, which claims priority to U.S. Provisional Application Ser. No. 62/738,572, filed Sep. 28, 2018, the contents of which are hereby incorporated by reference in their entirety.

FIELD OF INVENTION

The present invention is generally directed to the field of fundus imagers. More specifically, it is directed to a low cost fundus imager of improved field of view.

BACKGROUND

Various different types of image-capture devices for imaging a sample under test are known. Of particular interest are imaging systems capable of taking close-up images of a specimen with sufficient detail, e.g., sufficient focus, lighting, magnification, and signal-to-noise ratio (SNR). An example of such an imaging system is a fundus imager, which is typically used to image the fundus of an eye. The fundus is the interior surface of the eye opposite the eye lens (or crystalline lens) and may include the retina, optic disc, macula, fovea, and posterior pole. Two categories of imaging systems used to image the fundus are flood illumination imagers and scan imagers. Scan imagers may further be divided into confocal point scanning fundus imagers and line scanning imagers.

Flood illumination imagers flood with light an entire field-of-view (FOV) of interest of a specimen at the same time, such as by use of a flash lamp, and capture a full-frame image of the specimen (e.g., the fundus) with a full-frame camera (e.g., a camera having a two-dimensional (2D) photo sensor array of sufficient size to capture the desired FOV, as a whole). For example, a flood illumination fundus imager would flood the fundus of an eye with light, and capture a full-frame image of the fundus in a single image capture sequence of the camera.

FIG. 1 is a conceptual illustration of a flood illumination fundus imager 10. A flash-tube 15 is shown as an illumination source, whose illumination light follows an optical path along illumination axis 17, which may include various system lenses 19, and is folded by mirror 23 onto optical axis 25, which includes system lens 11, to be conveyed to the sample, or specimen, to be imaged (e.g., retina 33 of eye 13 in the present example). System lens 11 is the imager lens closest to the eye 13, and may herein be termed an ocular lens or ophthalmic lens. Optical axis 25 traverses the optical components of the eye 13 (including the cornea 27, iris 28, pupil 29, and crystalline lens 31) to reach the retina 33. Thus, illumination light traveling along optical axis 25 may enter the eye 13 through its cornea 27, pass through its pupil 29, and traverse crystalline lens 31 to flood the retina 33 with light at the back of the eye (e.g., the fundus area), and be scattered by the retina 33 (and other parts of the fundus). Scattered light returning from the fundus may exit through the crystalline lens 31, pupil 29, and cornea 27, and travel along optical axis 25 to a viewing axis 35. Viewing axis 35 may include multiple system lenses 21, and directs the scattered light returning from the fundus to a full-frame camera 37 (e.g., a detector), which includes a 2D photosensitive area. For example, the 2D photosensitive area may be embodied by a 2D sensor array of photosensitive elements (e.g., photocells, photodiodes, phototransistors, etc.). The entire field-of-view (FOV) 38 of the fundus is captured as a whole by the 2D sensor array to produce a full-frame image 39 of the fundus of the eye 13. Since viewing axis 35 and illumination axis 17 are coincident along optical axis 25, mirror 23 typically has a centrally located aperture 43 used to permit scattered light returning from eye 13 to pass through mirror 23 onto viewing axis 35 to be captured by camera 37. Mirror 23 may be flat and annular (e.g., ring-shaped) with round aperture 43 at its center. Mirror 23 may further be imaged to the pupil 29 if it is used for pupil splitting.

Pupil splitting permits illumination light (light entering the eye 13) and returning light (scattered light exiting the eye) to follow different paths into and out of the eye 13, at optimally chosen regions of the pupil. These regions may be chosen, for example, to avoid pupil clipping (e.g., avoid part of the light from being blocked/clipped by the iris 28 whose center defines the pupil 29), light scattering due to cataracts (e.g., clouded regions of the crystalline lens 31), and specular reflections (e.g., reflexes) from the cornea 27, such as due to the illumination light. To ease implementation of pupil splitting, mirror 23, which reflects illumination light towards the eye 13 and whose aperture 43 permits passage of returning light to the camera 37, may be imaged to (e.g., be on conjugate plane with), or near, the pupil 29. For example, when mirror 23 folds (e.g., reflects) illumination light from illumination axis 17 onto optical axis 25 towards eye 13, an annular-shape illumination region (or illumination ring) may be created at the eye 13 (e.g., near the pupil 29) due to the mirror's rounded aperture 43. That is, round aperture 43 of mirror 23 may create a round, non-illuminated region near the cornea 27 at the center of the annular-shape illumination region. Scattered light may exit the eye 13 through this non-illuminated region and thereby avoid mixing with the illumination light entering the eye 13.

Another source of image artifacts are reflexes (e.g., light reflections) at various system lenses. For example, reflex artifacts at the ophthalmic lens 11 created by the illumination light as it passes through ophthalmic lens 11 can be of particular concern. Such specular artifacts from system optical surfaces may be reduced by using so-called dark spots, which are stationary in illumination paths and carefully positioned to prevent certain surface areas of system optics from being illuminated. The need to eliminate reflexes may place constraints on the system which may limit its FOV. An example of a flood illumination imaging system is found in U.S. Pat. No. 3,915,564, assigned to the same assignee as the present invention, and herein incorporated in its entirety by reference.

By contrast, a confocal point scanning fundus imager uses a coherent point beam of light that is scanned both vertically and horizontally across a desired FOV of a sample (e.g., the fundus), and image-captures one point-illuminated portion, or spot, of the fundus at a time. That is, the desired, full FOV is not captured as a whole in a single image capture sequence of a camera. Rather, as the point beam is scanned across the sample, illuminating a different point of the sample at each scanning step, the returning (e.g., refracted or reflected) light passes through a pinhole to reach a single, predefined location on a photodetector that captures a point-portion (e.g., a pixel of image data) of the sample at a time (e.g., at each scanning step). The pinhole helps to eliminate out-of-focus light signal by allowing only the center of the returning light beam to reach the photodetector (e.g., the outer, diffused portion of the returning light beam is blocked). The returning light reaches the same point-location on the photodetector irrespective of scan position of the scanning point beam on the sample, and many individual point-portions (e.g., pixels of image data) need to be captured in sequential image capture sequences of a camera to create a full frame image. The many, captured point-portions resulting from one full scan of the desired FOV of the sample are combined to create a composite image, which may constitute a full-frame image.

Due to the point confocal arrangement of illumination and detection, the confocal point scanning fundus imager may advantageously suppress stray-light and out-of-focus light, and thereby produce high contrast images without the need for pupil splitting. Thus, a benefit of the confocal point scanning fundus imager over the flood illumination fundus imager is an increased level of confocality, which provides greater discrimination against undesirable light scattered from surfaces other than the target point to be imaged. However, since the confocal point scanning fundus imager operates with point illumination, it may require high intensities which raise safety issues when imaging a retina. Similarly, since much of the retuning light from the sample is blocked by the pinhole leading to the photodetector, its increased resolution is generally at the cost of decreased signal intensity so that its exposure time may need to be elongated. Additionally, the confocal point scanning fundus imager generally requires multiple scanning components (e.g., multiple galvanometers, or galvos) to achieve horizontal and vertical scans, which can be expensive and complicated, and can slow their image production since many points need to be collected to construct a full-frame composite image. This also may raise issues of eye movement during the collection of an image, which may lead to image distortion.

A line scanning imager may be thought of as a combination of a confocal point scanning imager and a flood illumination imager. A line scanning imager illuminates a linear region of a sample (e.g., the retina) at a time. This line of illumination defines a scan line that may span from one end of a desired FOV to its opposite end. The scan line may be scanned (e.g. traversed) across the sample (e.g. vertically or horizontally), and thereby illuminates the entire FOV in one sweep. A detector (e.g., camera) images the scan line at multiple scan positions as it is scanned across the sample, and a composite full-frame image may be constructed by combining the multiple, imaged, scanned positions.

The line scanning imager may use a narrow line beam (e.g., the laser-line scanning imager) or a broad line beam (e.g., the broad-line scanning imager) to scan a sample one line at a time. In the field of fundus imagers, the line scanning imager may be termed a line scanning ophthalmoscope, and includes both the line-scanning laser imager/ophthalmoscope, LSLO, which is an example of a laser-line scanning imager and typically uses a laser to produce a very narrow traversing line across a sample as it scans, and the broad-line scanning (fundus) imager/ophthalmoscope, BLFI, which is an example of a broad-line scanning imager and may use a non-coherent light source to produce a traversing broad line of predefined width across a sample as it scans. U.S. Pat. No. 7,768,652, which is herein incorporate in its entirety by reference, provides a description of an LSLO. Examples of broad-line scanning imagers may be found in U.S. Pub. No. 2017/0049323 and U.S. Pub. No. 2018/0014727, both assigned to same assignee as the present invention and both herein incorporated in their entirety by reference. Hereinafter, the term line scanning imager may be understood to refer to both, or either, of a laser-line (or very narrow-line) scanning imager (e.g., LSLO) and a broad-line scanning imager (e.g., BLFI).

FIG. 2 illustrates a line scanning imaging system 100 in a so-called "scan-descan" scanning configuration, wherein a scanning line beam 115 is scanned across a sample (e.g., retina 73 of eye 75), but a line of returning (e.g., scattered) light on a collection (optical) path 139 from the eye 75 is maintained at a stationary, predefined position on a detector 131 and does not scan across the detector 131. A radiation source 101 (e.g. light source, such as a laser, lamp, or LED) produces an illumination line beam 103 (non-coherent light beam or laser beam). A radiation aperture 105, imaged to the sample surface that is to be imaged, may be placed in front of radiation source 101 to help shape the illumination line beam 103. In the case of a fundus scan imager, radiation aperture 105 may be imaged to the retina 73 of the eye 75.

Illumination line beam 103 may pass through one or more optics before reaching a scanning component 137. For example, the illumination line beam 103 may pass through a collimating lens 111 and a beam splitter (or beam divider) 133 to reach scanning component 137, which may take any of multiple different implementations, such as one or more mirror galvanometer, MEMS scanner, electro-optical deflector, and/or rotating polygon scanner. For example, if scanning component 137 is implemented as a mirror galvanometer, a mirror is made to rotate in order to scan the received illumination line beam 103 from beam splitter 133 in discrete steps (or in continuous, definable steps) to define a scanning line beam of radiation (e.g., scanning line beam 115) that defines illumination lines (e.g., scan lines) across the sample to be imaged (e.g., retina 73). Typically, a scan lens 117 and ophthalmic lens 119 is placed in the optical path between scanning component 137 and eye 75. Generally, the scan lens 117 receives a scan beam from scanning component 137 at any of multiple scan angles (incident angles), and produce scanning line beam 115 with a substantially flat surface focal plane (e.g., a collimated light path). Ophthalmic lens 119 may focus the scanning line beam 115 onto the retina 73 of eye 75 to image the fundus. That is, scanning line beam 115 creates a traversing scan line across the retina 73.

FIG. 3 illustrates a simplified pattern of scan lines as they may be produced on the subject being scanned. In the present example, the scan lines are scanned (e.g., traversed) vertically to produce multiple scan lines L1 to Li in a vertical scan pattern, V-scan. Line scanning imagers, in general, may maintain some level of confocal suppression of out of focus light perpendicular (e.g., along the Y-axis) to the scan line (L1 to Li), but lack confocal suppression along the line (e.g., along the X-axis). The scan lines may also be used to enhance imaging. For example, the sharpness of the edge of an illumination strip may be used to find an optimized focus for the line scanning system for the case where the illumination has not moved significantly during an acquisition by the detector (typically when the scan beam is being scanned in steps and is relatively motionless during an acquisition). Locations on the retina that are not illuminated may be detected (e.g., image captured) to evaluate background levels, e.g., stray light levels, coming from out-of-focus regions of the eye, and this background level may then be subtracted from a captured line image. Line scanning imagers have also been combined with pupil splitting (see for example Muller et al. U.S. Pat. No. 8,488,895, which is herein incorporate in its entirety by reference).

Returning to FIG. 2, at each scan step (e.g., as defined by individual scan lines L1 to Li in FIG. 3), light is reflected/scattered back (in a capture phase) to scanning component 137. For purposes of discussion, scanning component 137 may be assumed to be substantially stationary during this capture phase, and so reflects the returning light along a similar optical path 135 as the illumination line beam from beam splitter 133, as illustrated by dual-headed arrows on optical path 135. The retuning, stationary line of scattered light is directed by beam splitter 133 onto a collection path 139, which conveys it to the photodetector 131, herein illustratively implemented as a line-scan camera. As shown, scanning component 137 maintains the location of returned scattered light on collection path 139 substantially stationary irrespective of the vertical scan position of scan lines L1 to Li on retina 73, which is herein termed a "descan" operation. That is, scattered light exits eye 75, and returns through ophthalmic lens 119, scan lens 117, to reach scanning component 137. Because the scanning position of scanning component 137 when returning light reaches it is substantially similar the position when a corresponding scanning line beam 115 was defined, scanning component 137 has the effect of "descanning" (or un-scanning) the returning light so that it is a steady line beam (non-scanning) by the time it is on optical path 135 and reaches beam splitter 133. At beam splitter 133, the returning light may be directed onto another focusing lens 121, which focusses the returning light beam onto photodetector 131. Each returning (scattered) light line is separately imaged (e.g., captured or detected) by the photodetector 131, as the scan line is scanned across the retina 73. Each captured returning light line from each discrete scan step may be mapped to a buffer 141 to define a separate buffered line image B1 to Bi at positions corresponding to the scan positions of their corresponding scan line L1 to Li (see FIG. 3). The buffered line images may then be reconstructed (e.g., montaged or stitched) into a full frame image 84, such as by use of a CPU 83 and rendered on a computer display 85. That is, the signal (e.g., line of light) that is detected by the photodetector 131 may be processed by CPU 83 to form full frame image 84, which may be displayed of video display 85, or stored in a memory associated with CPU 83 for further processing.

As can be seen from the above discussion, design and construction of a fundus imager can be complicated and expensive, requiring many components and consideration of multiple sources of image artifacts.

It is an object of the present invention to provide a low cost fundus imager.

It is another object of the present invention to provide a fundus imager with reduced reflex error.

It is a further object of the present invention to provide a fundus imager that provides a comparatively larger field-of-view without the complexities of a scan imager.

SUMMARY OF INVENTION

The above objects are met in a fundus camera optimized to use low cost components, and whose configuration avoids some traditional sources of image artifacts. Additionally, the traditional field-of-view (FOV) is expanded by combining two or more images of different FOVs into a composite image with a larger overall FOV. A first option is to use one or more light emitting diodes (LEDs) as light sources (e.g., miniaturized LEDs and/or high brightness LEDs). These LEDs may be imaged to an eye pupil and located near the camera's imaging stop but laterally offset, which allows the same optics to be used for illumination and detection. This eliminates the need for optics that would traditionally be needed to introduce the light source's optical path to the camera's optical path. Additionally, this positioning of the light sources may be used as part of a pupil splitting design to reduce the amount of reflection artifacts from the eye's optic elements, such as from the crystalline lens and cornea. Nonetheless, it was found that in spite of the use of pupil splitting, reflection artifacts from the cornea (e.g., cornea reflexes) may be encountered as one expands a desired FOV. Optionally, these cornea reflexes may be used as an alignment aid because they will move around as the fundus camera is moved during alignment. Nonetheless, cornea reflexes may be removed from a final captured image by actuating multiple LEDs separately, and capturing a separate image with each actuated LED. The location of an LED's reflection artifacts is related to its position relative to the camera's imaging stop. Thus, by capturing multiple images with LED's at different positions, one can obtain multiple images with reflection artifacts at different positions. Artifact-free regions from each image may be extracted and combined to construct an artifact-free, final image with larger overall FOV.

Another source of reflection artifacts is from system lenses, and in particular from the ophthalmic lens. Reflection artifacts due to system lenses may be avoided by removing all lenses from the pupil relay (e.g., the optical path between the camera's imaging stop and the pupil of eye being imaged). The pupil relay may instead by constructed using only curved reflective surfaces (e.g., mirrors).

The cost may further be reduced by introducing a combination camera that incorporates both a pupil camera (or iris camera) operation and retina camera operation. Two approaches are provided. One embodiment essentially inserts a retina camera within the pupil camera, both having a similar optical path. In this case, a focus lens of the pupil camera has an aperture through which the retina camera may be inserted. The inserted retina camera captures an image of the fundus on a first region of a first sensor array, and the outer portion of the pupil camera's focus lens focuses the pupil (or iris) onto a second region of a second sensor array behind the first sensor array. The image from the second sensor array includes a shadow region produced by the retina camera, but this shadow region may be used to align the present fundus camera to the patient. For example, when the shadow region is within the center region of the pupil/iris image produced by the second sensor array, the fundus camera may be deemed to be aligned (e.g., within an x-y plane). Another embodiment combines the first and second regions onto a single sensor array. This single sensor array extends beyond the perimeter of the retina camera. That is, the single sensor array is divided into the first region, on which the image of the retina is captured, and the second region on which the image of the pupil/iris is captured. As a result, both the pupil and retina are visible (e.g., imaged) on a single image from this single sensor array, with minimal, if any, shadow between them.

Cost may further be reduced by introducing a mechanism for self-alignment. That is, traditionally, an operator is needed to monitor the patient's pupil and align the fundus camera prior to taking an image of the patient's retina. Alternatively, automated feedback mechanisms have been used to monitor the patient's pupil for alignment. Providing a self-alignment mechanism for the patient's use eliminates the need for, and cost of, these traditional approaches. In embodiments, this may be achieved by introducing a curved reflective surface (e.g., mirror) behind the retina camera, wherein the curved reflective surface directs a view of the outside of the eye (e.g., the pupil or iris) to the eye being examined. The patient thus sees an image of his pupil/iris with a shadow region corresponding to the position of the retina camera. The patient may then adjust their position (or adjust the fundus camera's position) to bring the viewed shadow region into the center of the viewed pupil/iris, and thereby align the fundus camera for imaging the retina.

The present objects are met in an ophthalmic diagnostic system for imaging an eye (e.g., a fundus imager), including a detector (e.g., camera) for capturing an image of the eye, and at least a first and second light source (e.g., high brightness LED) placed proximate (e.g., adjacent) the detector's aperture (e.g., imaging stop), such that both the detector and light sources share a similar optical path toward/from the eye (e.g., pupil relay) and both are conjugate to the pupil of the eye. That is, LEDS are located near, but laterally offset from, the imaging stop, which allows the same optics to be used for illumination and detection. The detector captures a first image of the eye (e.g., the fundus region of the eye) with the first light source actuated and the second light source not actuated, and captures a second image of the eye with the second light source actuated and the first light source not actuated. As explained above, each light source may produce a reflex artifact region at a different location on the captured image. A data processor may be used to extract a first section of the first image excluding reflection artifacts, such as caused by the first light source, extract a second section of the second image excluding reflection artifacts, such as caused by the second light source, and combine the first and second sections to construct a composite image. The composite image thus avoids the reflection artifacts due to the first and second light sources, and further recovers the FOV that had been previously blocked by these reflection regions. Thus, the composite image is a reflex-free image of larger FOV than either of the first or second image.

Optionally, a third light source (e.g., LED) may be placed proximate to the detector's imaging stop. As it would be understood, the first and second light sources illuminate the retina of the eye, but this third light source may be used primary to illuminate the outside (e.g., pupil/iris) of the eye. The third light source may be an infrared light source, which is invisible to a patient, in order to avoid patient discomfort or pupil reaction from the patient. However, since illumination from the third LED may be maintained outside the eye, the third light source may optionally also be visible light. When using additional light sources to image the pupil, the detector may be made to have a first imaging region conjugate to the retina of the eye and a second imaging region conjugate to the pupil of the eye. For example, the detector may include a first photo-detector array in front of a second photo-detector array along an axial optical path of the detector, and the first imaging region may be within the first photo-detector array and the second imaging region may be within the second photo-detector array. This may be achieved by providing a detector lens having an outer region surrounding a central aperture along the axial optical path of the detector, where the aperture is sized to prevent the detector lens from receiving (or minimizing the amount of received) reflected light from the retina of the eye. The outer region may then focus reflected light from the pupil of the eye onto the second imaging region of the second photo-detector array. This may be implemented, for example, by having the first photo-detector array be part of a first camera unit, and having the second photo-detector array be part of a second camera unit, and having the first camera unit inserted within the central aperture (e.g., of the second camera unit). Alternatively, the first imaging region and second imaging region may be defined within a single photo-detector array.

To implement self-alignment, a curved reflector may be positioned at least partially surrounding the detector and directed towards the eye. In this manner, the reflector provides a patient-viewable image of the eye to the same eye being imaged (e.g., examined). The patient-viewable image of the eye is indicative of an alignment of the detector to the eye, which the patient may use to adjust alignment of the fundus camera.

Optionally, the pupil relay between the detector and the eye may have no lenses. This avoids any reflections from such lenses. Instead of lenses, a first curved reflector separated from a second curved reflector may be used to define the pupil relay. The first curved reflector may receive light from the first and second light sources at a first field-of-view (FOV), and reflect the received light to the second curved reflector, which reflects this received light at a second FOV to the eye. The second FOV may be greater than the first FOV. One may compensate for refractive error in the eye by adjusting the separation between the first curved reflector and second curved reflector.

In another embodiment, an ophthalmic diagnostic system for imaging an eye of a patient (e.g., a fundus imager) includes a detector for capturing an image of the eye, at least one light source proximate (e.g., adjacent) to the detector aperture such that both share the same optics for illumination and detection, and a curved reflector at least partially surrounding the detector and directed towards the eye. The reflector is configured to provide a patient-viewable image of the eye to the same eye that is to be imaged. The patient-viewable image is indicative of an alignment of the detector to the eye, and may be used by the patient to self-align the detector to the eye's pupil.

In this implementation, the curved reflector may be positioned behind the detector on an optical axis of the detector. Consequently, the patient-viewable image may include an image of the eye's pupil/iris with a shadow region corresponding to a position of the detector. The detector may then be aligned to the eye's pupil by aligning the shadow region to a central region of the image of the eye's pupil/iris. For example, a user-input for controlling movement of the detector within at least one plane of motion may be provided. The patient may then use the user-input to self-align the detector to the iris.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Any embodiment feature mentioned in one claim category, e.g. method, can be claimed in another claim category, e.g. system, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts.

DESCRIPTION OF THE PREFERRED EMBODIMENTS

Figure 1:
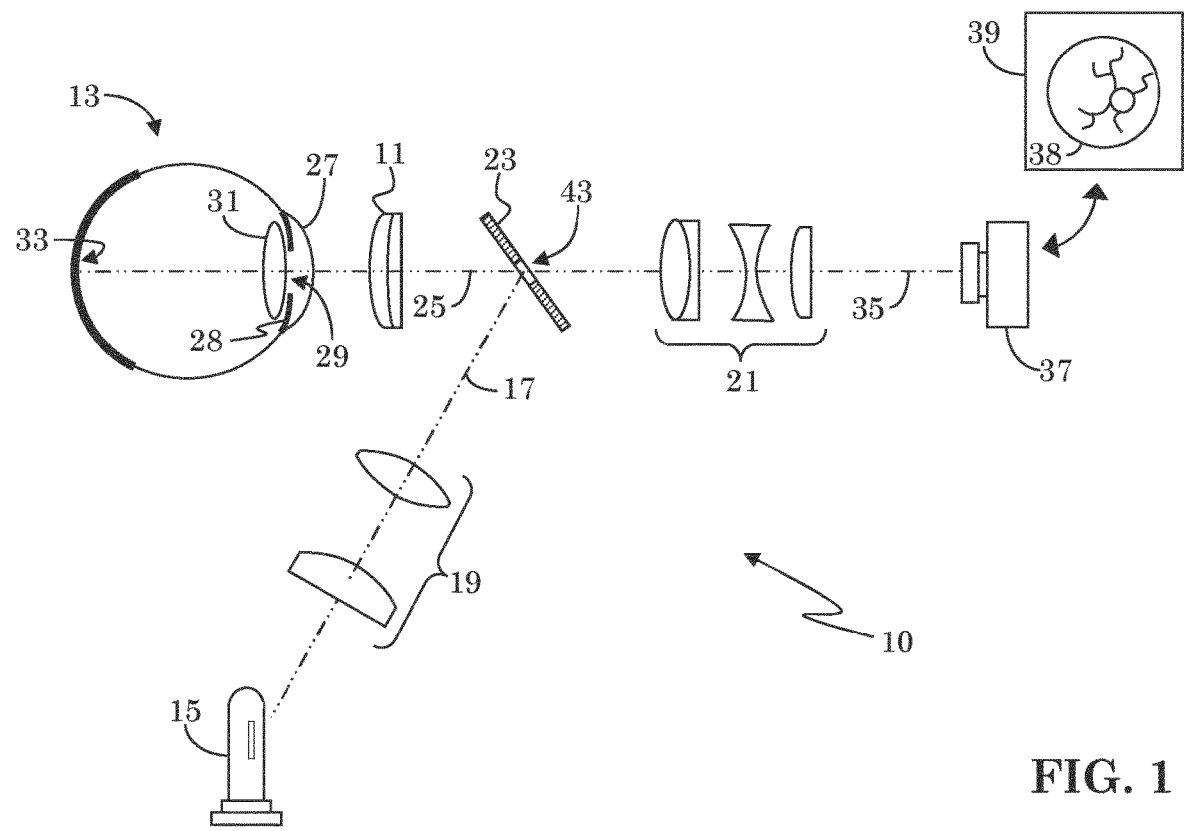
FIG. 1 is a conceptual illustration of a flood illumination fundus imager.
Figure 3:
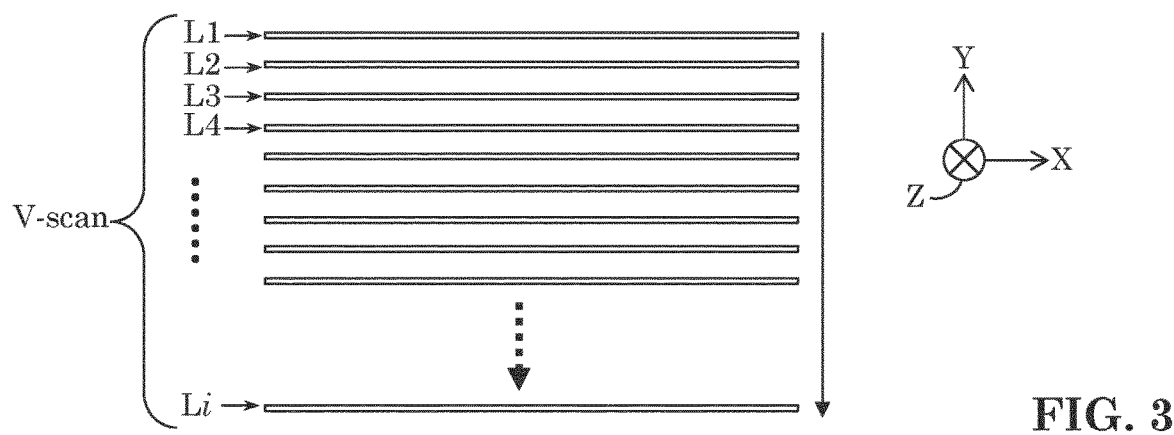
FIG. 3 illustrates a simplified, exemplary scanning pattern for a line scanning imager.
Figure 2:
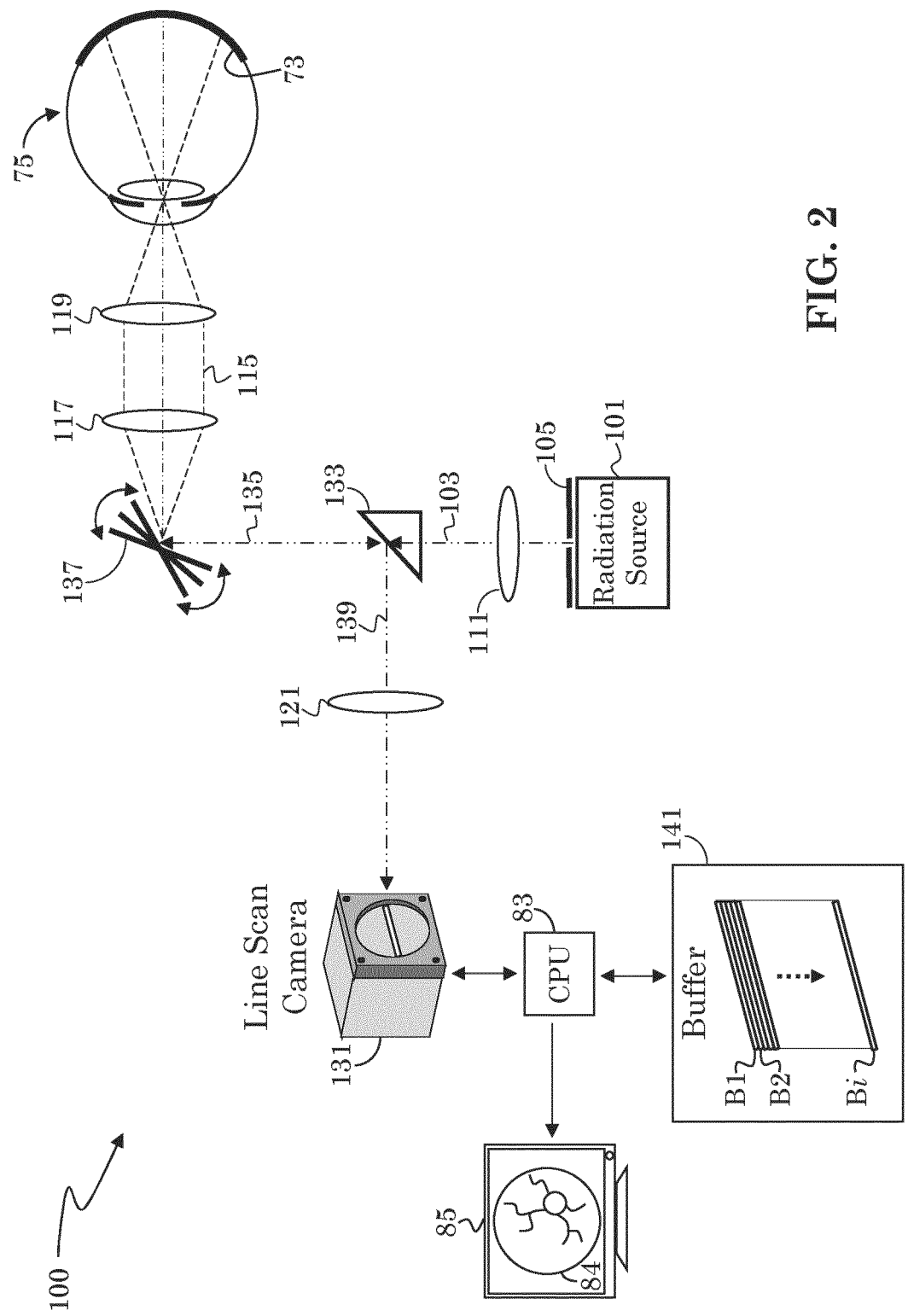
FIG. 2 illustrates an idealized scanning configuration of a so-called "scan-descan" line scanning imaging system, wherein a scanning line beam is scanned across a sample, but a line of returning light on a collection optical path from the eye is maintained at a stationary, predefined position on a detector and does not scan across the detector.

Fundus imaging is a well-established diagnostic tool in ophthalmology. A fundus camera delivers the illumination light to the back of the eye and collects the light that is reflected back. The primary challenge that any fundus camera has to overcome is to create an artifact-free image by avoiding or eliminating reflections off lenses in the fundus camera and the cornea of the human eye.

A secondary task of the fundus camera system is to aid in patient alignment or pupil alignment when coupled with another ophthalmic instrument. For example, an optical coherence tomography (OCT) system may include a fundus camera, and may make use of the fundus camera to assure proper alignment of the patient and the OCT system prior to initiating an OCT scanning operation. That is, the fundus camera may provide a real time view of the patient's eye which an OCT operator may use to assure that a desired area of the fundus is in view prior to activating an OCT scanning operation.

As stated, a challenge of fundus cameras is to overcome image artifacts, such as due to light reflections from lenses. Current fundus cameras may use pupil split optics to implement pupil splitting. The pupil provides a limited area through which light enters and exits an eye. Pupil splitting designates a first pupil region through which illumination light enter the eye, and a second pupil region through which reflected light exiting the eye is directed to a detector, and attempts to maintain these two regions separate from each other. Another technique for reducing system lens reflection (used in flood illumination fundus cameras) is the use of anti-reflection dots on specific lenses. As explained above, confocal point scanning fundus imagers and line scanning imagers may employ additional techniques to remove image artifacts. These techniques help to avoid, or mitigate, reflections off the human cornea and/or off system lenses in a fundus camera, but introduce additional complexity and cost to the fundus camera.

Another technique for reducing lens reflections is to reduce the use of lenses, e.g., refractive optics. In place of refractive optics, one may use reflective optics, such as mirrors, when possible. Fundus cameras using reflective optics have been demonstrated previously, see for example, German published application DE 10 2011 114753 A1 assigned to Carl Zeiss Meditec AG, and herein incorporated in its entirety by reference.

Some fundus cameras provide an iris (or pupil) camera to aid in pupil alignment. That is, the iris camera may be used to provide a real-time view of the iris, whose center defines the pupil. By viewing the iris, an operator may align the fundus camera to the pupil to assure unobstructed access to the fundus area of the eye, and thereby avoid additional error such due to pupil clipping.

The present invention provides a low cost, artifact-free, fundus camera using one or more (e.g. high brightness) LEDs for illumination, which may be placed in the same (or substantially similar) plane as, but laterally offset from, the imaging stop (e.g., pupil stop or detection stop, or detection aperture) of the fundus camera to act as a pupil-split design/mechanism. Reflective optics may be used to relay the pupil split to the pupil of the human eye, and thereby avoid reflection artifacts that may have arisen from the use lenses, such as from an ophthalmic lens, when illuminating the eye.

Although pupil splitting may reduce reflection artifacts from the cornea, it has been found that as the FOV is expanded, artifacts from the cornea may still be encountered, which limit the achievable FOV. That is, a reflection footprint corresponding to an illumination LED may be imaged by the detector, and the footprint area reduces the FOV of the captured image. Thus, the FOV may be increased by eliminating this footprint area. One approach for achieving this is to use two or more LEDs on (or substantially near) a plane of, but laterally offset from, the detector's imaging stop, with each LED actuated separately and a separate image captured for each actuated LED. The image from each actuated LED may include that LED's reflection footprint, but this footprint will be at a different position for each LED in each captured image, depending upon the position of the LED relative to the imaging stop. Thus, the area of a first LED's reflection footprint in a first image may be clear of any reflection footprint in a second image corresponding to a second LED at a second position. The first and second images may therefore be combined with their respective LED reflection footprint removed to construct a composite image with no LED reflection artifacts. For example, a first LED may be placed on one side of the camera's imaging stop and a second LED may be placed at an opposite side of the imaging stop. A first image captured with only the first LED actuated will show that LED's reflection footprint on one side of the image. A second image taken with only the second LED actuated will show that LED's reflection footprint on an opposite side of the image. The artifact-free portion of the first image may be combined with the artifact-free portion of the second image to construct a composite, artifact-free, third image with a larger FOV than either of the first or second image.

Optionally, the fundus imager may further provide an integrated iris viewer (e.g. iris camera or pupil camera) to aid in pupil alignment. The iris viewer may be on the same, or similar, optical axis as a first sensor housing whose detection aperture is the above-mentioned imaging stop and which includes a first sensor (e.g., photosensor array). This imaging stop may be conjugate to the eye pupil and be sized to receive a projection of the eye fundus through the eye pupil for imaging the fundus onto the first sensor. Any LED may be positioned on the first sensor housing on a similar plane as, and offset from, (e.g., adjacent or near) its imaging stop. Preferably, the size of the first sensor housing is made similar to its imaging stop so that any projection of the iris is permitted to pass around the first sensor housing. A second sensor may be positioned behind, and on (e.g., substantially) the same (or similar) optical axis as, the first sensor so as to capture an image of the iris projection that passes round the first sensor housing. As it would be understood, the captured image of the iris would have a dark (e.g., shadow) region corresponding to the position of the first sensor housing (and any LEDs), but this darken region may be used to align the fundus imager by assuring that the darken region is at the center of the imaged iris.

Optionally, the second sensor may be part of a second sensor housing having a second aperture. In this case, the first sensor housing may be inserted within a central region of the second aperture. A focusing lens of the second sensor housing may have an aperture through which the first sensor housing is inserted. An outer area of this focusing lens may focus onto the second sensor the portion of the projection of the iris that pass around the first sensor housing. This may provide for a more compact configuration.

Alternatively, the first and second sensors may be combined into a single combination sensor. In this embodiment, the combination sensor would extend beyond the boundary of the first sensor housing, and a central portion of the combination sensor may be used to image the retina via the first sensor housing, and a perimeter portion of the combination sensor may be used to image the iris.

Optionally, a curved reflective surface may be placed behind the first sensor housing in place of (or in addition to) the second sensor. This curved reflective surface may be on the optical axis of the first sensor housing and directs an image of the iris back to the eye being imaged. In this manner a patient may see an image of his eye's iris along with a shadow region corresponding to his eye's pupil. The patient may then self-align the fundus image by maneuvering the observed shadow region to the center of the observed iris. For example, the patient may maneuver the observed shadow region by physically moving his head to better align the eye, or may maneuver the position of the first sensor housing to align to the eye by use of a graphic-user-interface (GUI) or computer input device (e.g., joy stick, computer mouse, roller, etc.).

The present fundus imager builds on the concept of a flood fundus imager. Fundus imaging is a photographic technology that takes photographs of the back of the eye. A flood fundus camera typically delivers a short flash of white light through the eye's pupil, and collects the reflected light by use of imaging optics to form an image. This image is recorded by a detector. The magnitude of the signal returning from the back of the eye is orders of magnitude lower than the illumination light. Any light reflected on an illumination path into the eye is imaged onto the detector (e.g., sensor) and creates undesirable reflection artifacts on the image. The reflections are typically much brighter than the fundus signal, thereby drowning out the clinical information in the fundus image.

Figure 4:
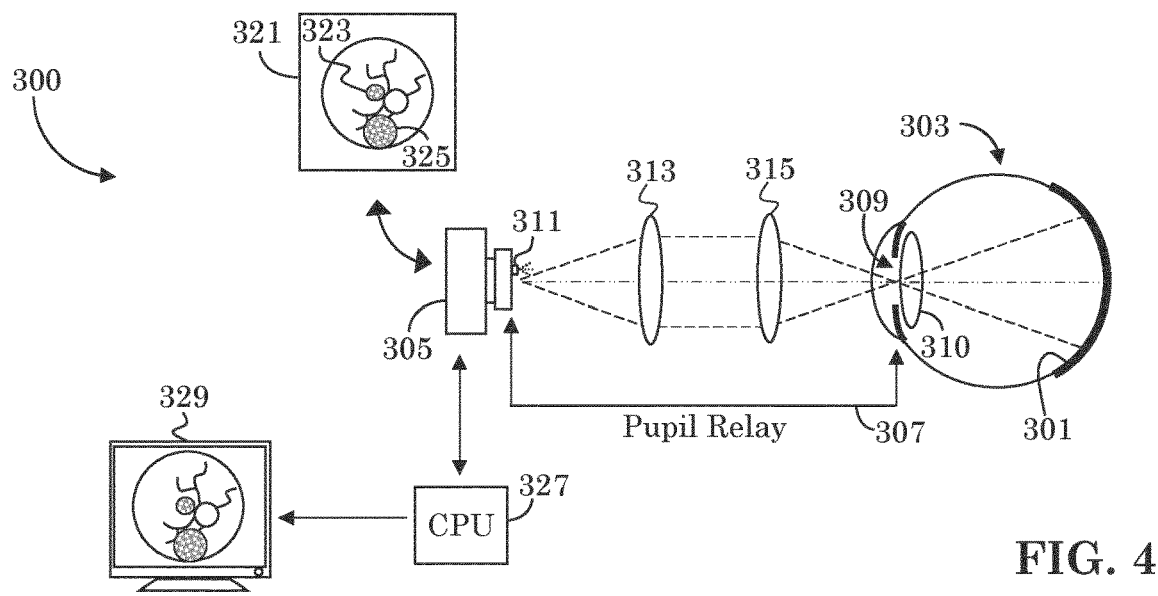
FIG. 4 illustrates a fundus imager for imaging the retina of an eye using a camera in accord with the present invention.

FIG. 4 illustrates a fundus imager 300 for imaging the retina 301 of an eye 303 using a camera 305 in accord with the present invention. As it is known in the art, camera 305 includes an imaging stop, or pupil stop, (not shown), which is an opening (e.g., aperture whose size may be variable) through which light enters the camera for imaging onto an internal sensor (e.g. photosensor, not shown). A pupil relay 307 provides an optical path that places the imaging stop of camera 305 conjugate to the pupil 309 of eye 303, and internal optics of camera 305 focus light entering the camera onto its internal sensor, which is conjugate to retina 301. In the present example, pupil relay 307 is implemented using two converging lenses 313 and 315 in a 4f configuration, as is known in the art, but other configurations for pupil relay 307 may be used.

A light source is positioned adjacent to the camera's imaging stop to provide flood illumination of the retina 301. In the present embodiment, a LED 311 is provided as the light source, but it is to be understood that other light sources may be used without deviating from the present invention. Because LED 311 is adjacent the imaging stop of camera 305, both are conjugate to the pupil 309, and both are maintained separate at the pupil 309. Consequently, the present configuration establishing a compact pupil splitting mechanism whereby illumination light from the LED 311 enters the eye 303 at a designated region of the pupil 309 different from another designated region of the pupil 309 through which exiting scattered (e.g., returning) light is directed to the imaging stop of camera 305 for imaging. It is noted that the present configuration establishes a pupil splitting design without the need of a secondary optical path 17 and annular mirror 23 of a traditional flood illumination fundus imager, as described above in reference to FIG. 1.

As is explained above, a main technical task in fundus imaging is avoidance or elimination of reflection artifacts. In the present embodiment, reflections off the human cornea may be mitigated by using the well-established approach of pupil splitting, where pupil splitting is implemented by placing one or more LEDs (or other light source) adjacent (optionally around) the camera's imaging stop. Nonetheless, reflection artifacts 325 from the cornea (e.g., cornea reflexes) may still be present, and as the field of view is increased, these reflection artifacts 325 may become evident in an image 321. Although typically considered an unwanted artifact, cornea reflexes 325 may be used as an alignment aid. They will move around as the fundus camera is moved such that may be use used as a marker, or indicator, for camera alignment. After alignment is achieved, cornea reflexes 325 may be avoided during that capture of a final retina (or fundus) image, as is explained below.

Additional, secondary reflection artifacts 323 may also be present in the image 321 due to system lenses, such as from ophthalmic lens 315. One way of reducing reflection artifacts 323 due to a system lens is by use of a so-called dark spot, as is explained above. Another way to avoid artifacts due to system lenses is to avoid the use of system lenses in pupil relay 307, as is explained below.

The captured image 321 may be transferred to a CPU 327 (e.g., computing system or device) for optional imaging processing and/or for displaying onto an electronic display 329.

Figure 5:
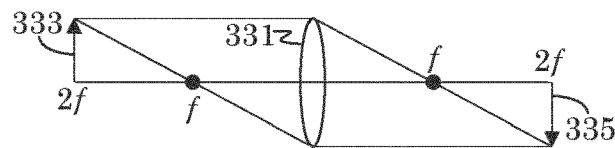
FIG. 5 illustrates a second configuration for the pupil relay of FIG. 4.

FIG. 5 illustrates another configuration for the pupil relay 307 of FIG. 4. That is, lenses 313 and 315 of FIG. 4 may be replaced by single lens 331 in a 2f configuration, as is known the art. Plane 333 (e.g., two focal points distance from lens 331) is conjugate to plane 335. Using the present pupil relay, the imaging stop of camera 305 may be on plane 333 and the pupil 309 of eye 303 may be on plane 335 within the configuration of FIG. 4.

Figure 6:
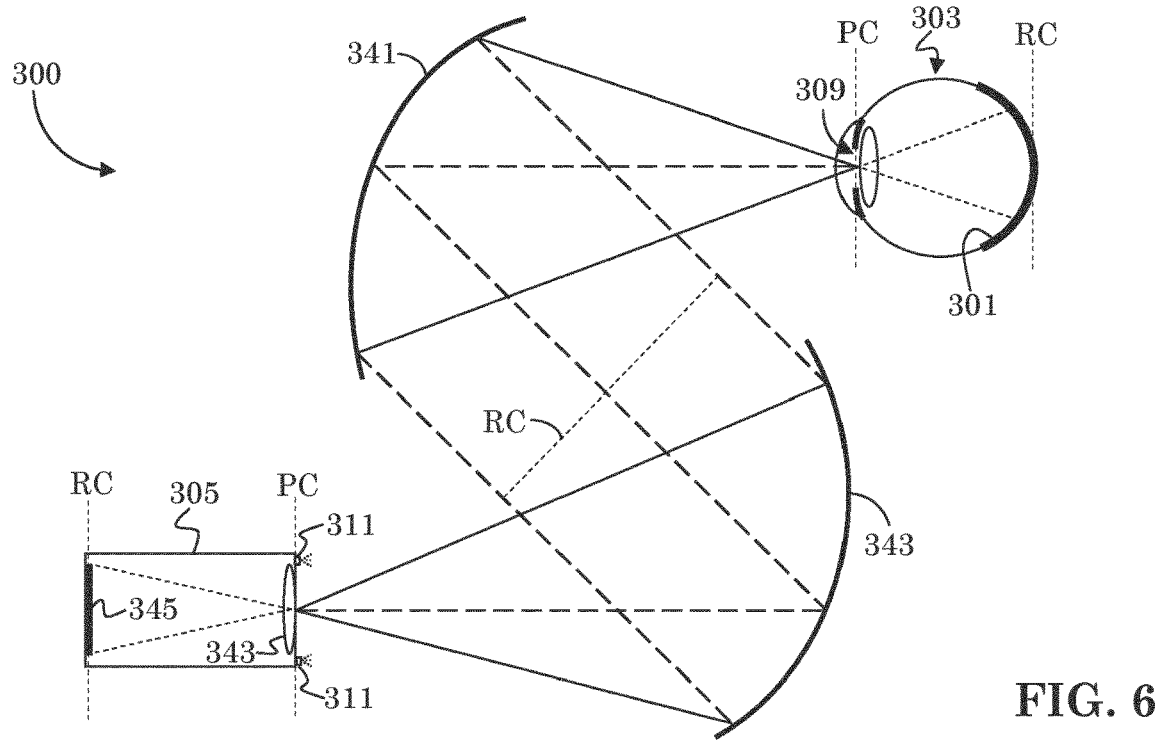
FIG. 6 illustrates an alternate configuration for the pupil relay of FIG. 4 using reflective elements in place of refractive elements.

FIG. 6 illustrates an alternate configuration for the pupil relay 307 (e.g., imaging path) of FIG. 4 using reflective elements in place of refractive elements (e.g., lenses 313 and 315). All elements similar to those of FIG. 4 have similar reference characters and are described above. Reference character RC indicates a retina conjugate plane, and reference characters PC indicates a pupil conjugate plane. For illustration purposes, camera 305 is illustrated as a rectangular sensor housing, and an internal schematic view of camera 305 illustrates a focusing lens 343 conjugate to pupil 309 and a sensor (photosensor array) 345 conjugate to retina 301. As shown, the camera 305 may have multiple light sources (e.g., LEDs 311) adjacent to, and distributed about, the camera's imaging stop, although only two LEDs are shown. For example, camera 305 may be configured as an endoscope camera with LEDs distributed about its imaging stop. In the present implementation, the pupil relay consists of a first curved reflective surface 341 and a second curved reflective surface 343. For example, the first curved reflective surface 341 may be a parabolic mirror, and the second reflective surface 343 may be a spherical mirror. The present optical system images the retina 301 onto the sensor 345 and images the pupil 309 of the human eye 303 onto the imaging stop (e.g., pupil split plane) of the camera 305.

By using reflective surfaces 341 and 343 and avoiding the use of lenses in the pupil relay between the camera 305 and the eye 303, reflection artifacts 323 due to system lenses is avoided. That is, back-reflections off the imaging optics are eliminated by using reflective optics. Optionally, the separation distance between reflective surfaces 341 and 343 may be made adjustable, and their separation may be adjusted to compensate for refractive error in the eye. Optionally, reflective surface 343 may be shaped such that it receives light from the LEDs 311 at a first FOV, and reflect the received light to the second reflective surface 341, which reflects this received light at a second, greater FOV to the eye.

Figure 7:
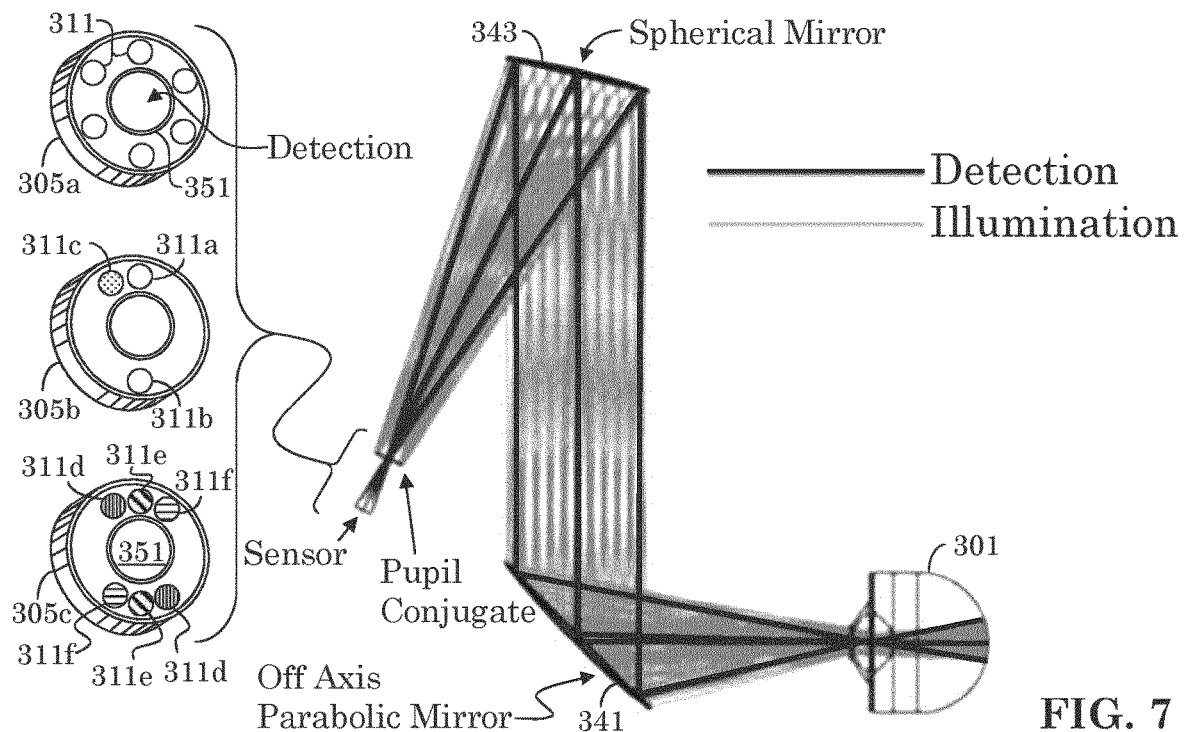
FIG. 7 illustrates a model view of light paths in accord with the configuration of FIG. 6.

FIG. 7 illustrates a model view of light paths in accord with the configuration of FIG. 6. Multiple configurations for camera 305 are shown. For example, camera configuration 305a shows a ring of LEDs 311 around the camera imaging stop 351 (e.g., the pupil of the imaging camera 305a). All the LEDs 311 in this ring may be actuated in unison for bright illumination, or each may be individually controlled so as to control the amount of illumination or the direction of illumination. That is, each LED 311 (or alternately, each select group of LEDs 311) may be actuated individually in sequence, and a separate fundus image may be captured for each illuminated LED (or each illuminated group of LEDs). As stated above, imaging stop 351 and LEDs 311 are at a pupil conjugate plane, and detection (e.g., image capture) of the retina is achieved by light returning from the eye 301 entering imaging stop 351 and being focused onto the camera's sensor. Camera 305a may also provide focusing to correct for refractive error of the human eye 301.

Alternatively, different types of LEDs may be provided adjacent the imaging stop of camera 305. For example, camera configuration 305b shows two visible light (e.g., white light) LEDs 311a and 311b, and a non-visible light (e.g., infrared) LED 311c. Like above, the LEDs 311a. 311b, and 311c may be actuated concurrently, or in any desired sequence or combination. For example, infrared LED 311c may be continuously activated/actuated to provide a continuous view of the iris of the eye 301, while LEDs 311a and 311b may be alternately actuated and a separate fundus image may be captured for each actuation of LEDs 311a and 311b.

In camera configuration 305c, the LEDs are separated into color groups. For example, two groups may be defined with each group including one red LED 311d, one green LED 311e, and one blue LED 311f. Color images may be captured by appropriate actuations of the color LEDs in each group. For example, all the LEDs within a color group may be actuated together. Alternatively, the LEDs in each group may be actuated separately, e.g., in sequence. Further alternatively, the groups may be defined by color, such that a first group may include the two red LEDs 311d, a second group may include the two green LEDs 311g, and a third group may include the two blue LEDs 311f. Each group may provide a separate image with a separate color, but within each group, the LEDs may still be actuated sequentially. For example, a composite red image may be constructed by capturing a first red image using only one actuated red LED 311d at one side of the imaging stop 351, capturing a second red image using only the second red LED 311d at another position relative to the imaging stop, and combining the two captured red images. As will be explained more fully below, this approach may help to further reduce reflection artifacts and increase the FOV.

Figure 8:
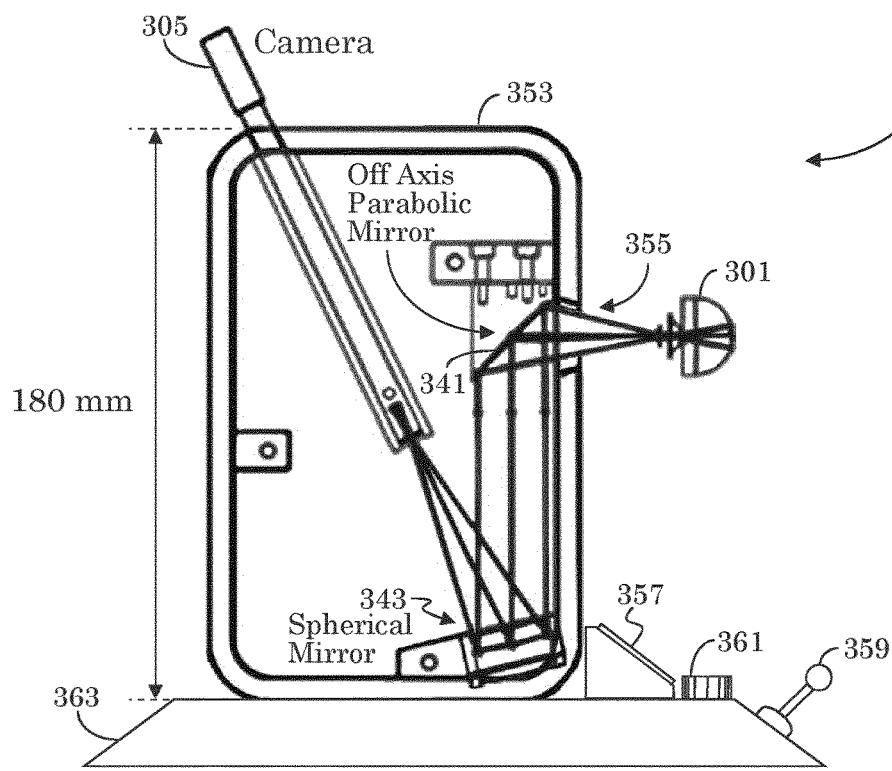
FIG. 8 illustrates an exemplary fundus imager construction in accord with the present invention.

FIG. 8 illustrates an exemplary fundus imager 300 in accord with the present invention. All elements similar to those of FIGS. 6 and 7 have similar reference characters and are described above. In the present embodiment, the pupil relay of FIGS. 6 and 7 is enclosed within a housing 353. An advantage of this configuration is the use of only a few low-cost components and simple assembly. For example, housing 353 may be a 3D printed housing, and fundus camera 300 may be constructed using three low cost components. Camera 305 may be (or be based on) an endoscope camera, which may cost as low as $40. Spherical mirror 343 and parabolic mirror 341 may be off-the-shelf components with prices of, for example, $50 and $100, respectively. These components can be easily mounted on the 3D printed housing 353.

Optionally, housing 353 may be mounted on a (maneuverable) table, or base, 363 for ease alignment of camera 305 to eye 301. Eye 301 may represent a patient's eye, and the relative position of housing 353 to eye 301 may be adjusted. For example, the patient may physically move so as to align eye 301 to camera 305 through an ocular view port 355. Alternatively, alignment may be achieved by moving fundus imager 300 such as by use of a graphics user interface 357 and/or a computer user input device, such as a joystick 359 and/or roller 361. Alternatively, fundus imager 300 may be small and light enough so that the patient may physically lift and position it for alignment.

The configuration of FIGS. 6, 7 and 8 eliminate reflection artifacts 323 due to system lenses (see FIG. 4), as explained above, but the FOV may still be limited by reflection artifacts from the cornea of the eye. As is also explained above, the present invention envisions individual control of multiple light sources (e.g., multiple LEDs), and artifacts due to reflections off the cornea may be eliminated by appropriate control of LEDs and appropriate combination of images from individual LEDs (or individual groups of LEDs).

Figure 9:
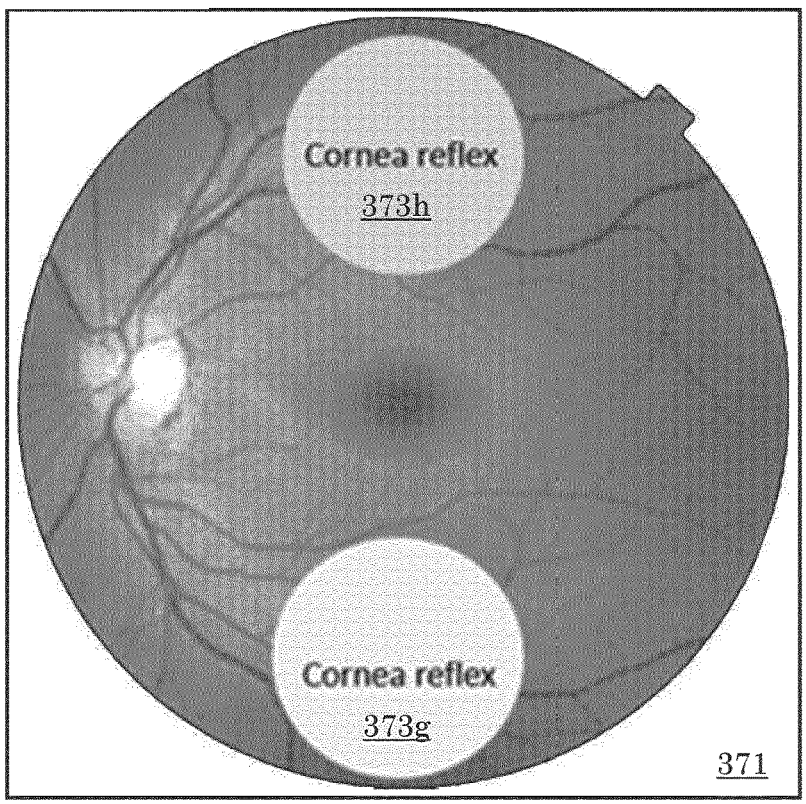
FIG. 9 illustrates an example configuration of a camera suitable for expanding the FOV of the present fundus imager.
Figure 9:
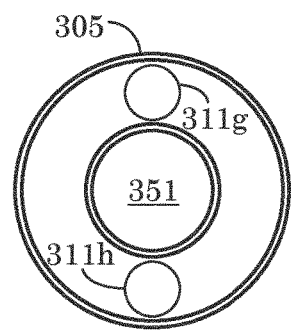

FIG. 9 illustrates an example configuration of camera 305 suitable for expanding the FOV of a fundus imager in accord with the present invention. For illustration purposes, camera 305 is shown having two LEDs 311g and 311h (each of which may be visible white light) on opposite sides of imaging stop 351, and a sample captured image 371 when both LEDs 311g and 311g are actuated concurrently. Each of LED 311g and 311h produces a respective, reflection artifact footprint (e.g., cornea reflexes) 373g and 373h, both of which limit the available FOV. However, by proper control of LEDs 311g and 311h, reflection artifact footprint 373g and 373h may be avoided (or removed) and an expanded FOV may be achieved. Prior to removing cornea reflexes 373h and/or 373g, however, either or both of cornea reflexes 373h and/or 373g may be used for camera alignment. For example, during a preview phase (or alignment phase), camera alignment may be adjusted until cornea reflexes 373g and 373h are clearly visible and/or a target retinal area is centered between cornea reflexes 373g and 373h. After alignment is achieved, a retinal image capture phase may be initiated in which cornea reflexes 373h and/or 373g are avoided/removed, as explained below.

Figure 10:
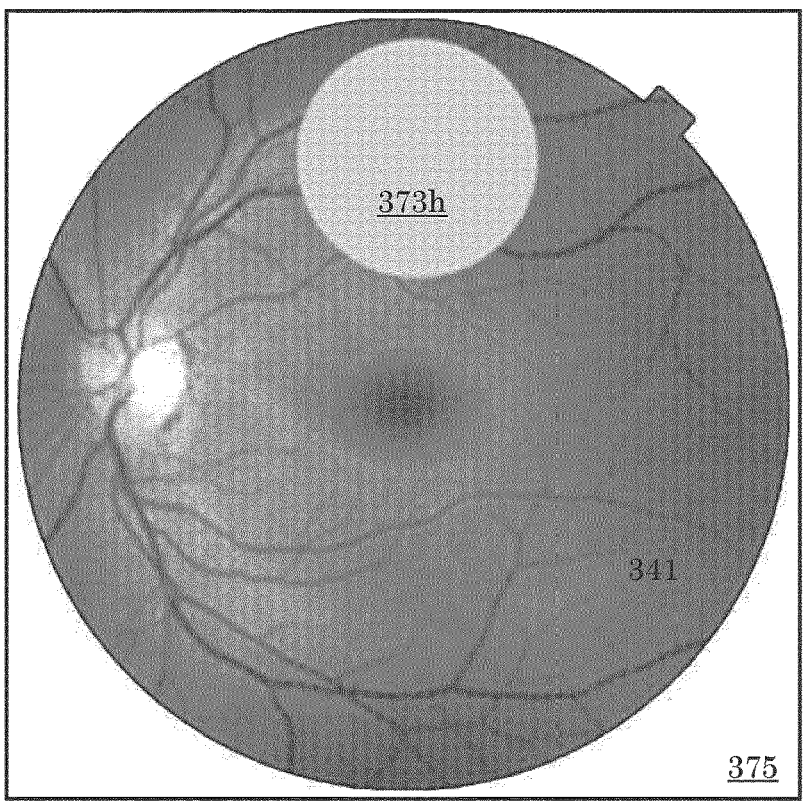
FIG. 10 illustrates a first captured fundus image resulting from select actuation of an individual LED from FIG. 9.
Figure 10:
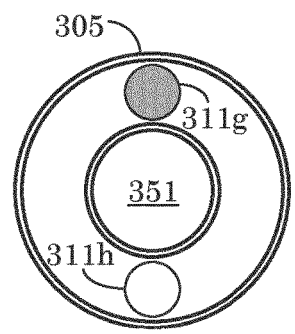

FIG. 10 illustrates a first captured fundus image 375 resulting from select actuation of an individual LED from FIG. 9. In the present case, LED 311h is actuated (turned on) while LED 311g is not actuated (e.g., turned off). As shown, this operation expands the available FOV of first captured fundus image 375 to include the lower hemisphere previously blocked by reflection footprint 373g in FIG. 9. As it would be understood, capturing another fundus image with LED 311g actuated while LED 311h is not actuated would result in a second captured fundus image with an artifact-free upper hemisphere, and a lower hemisphere with a reflection footprint from actuated LED 311g. By combining the artifact-free portions of the first and second captured fundus images, one may construct an artifact-free composite image.

Figure 11:
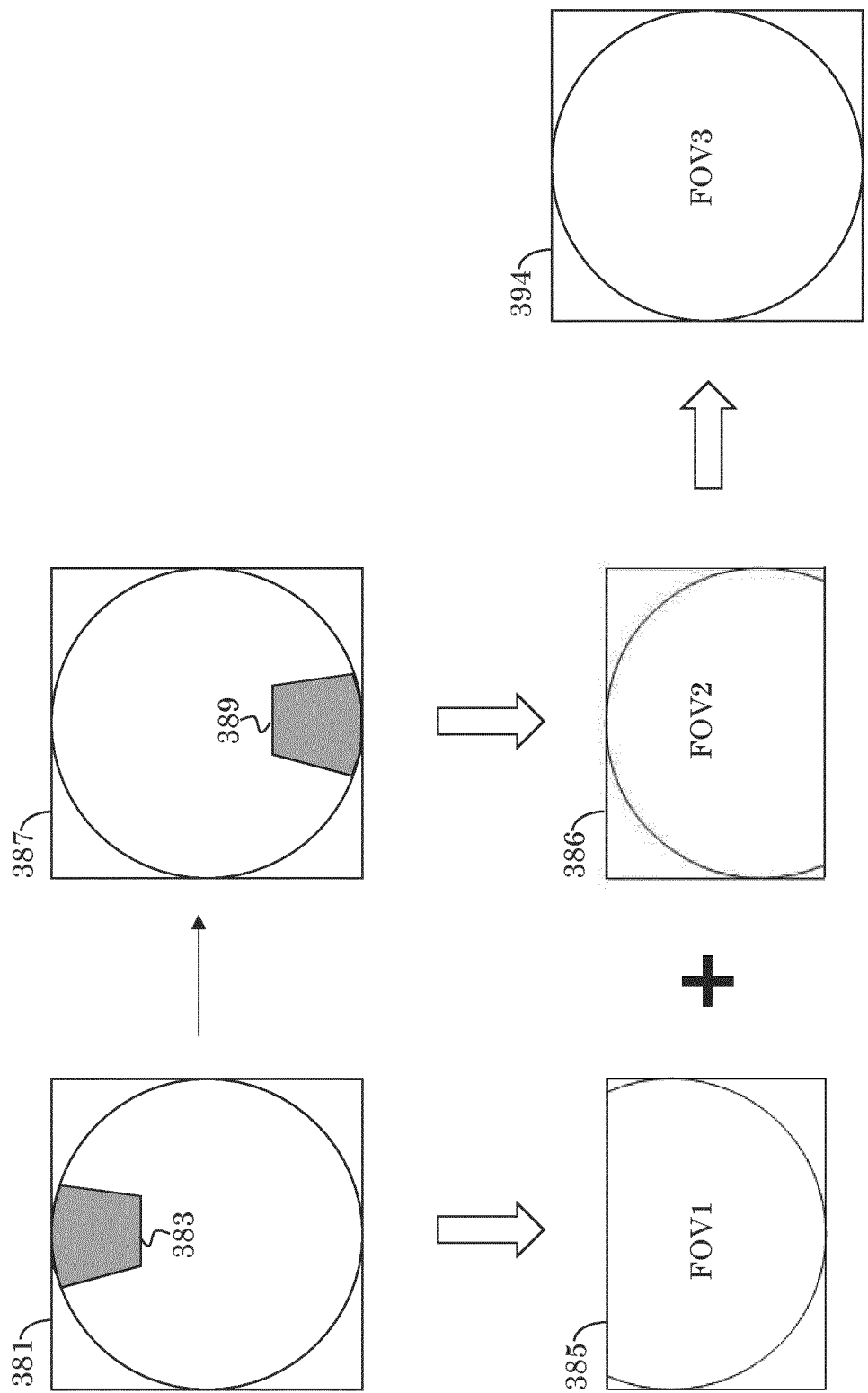
FIG. 11 illustrates a method for capturing artifact-free images using a camera in accord with the present invention.

FIG. 11 illustrates a method for capturing artifact-free images using a camera in accord with the present invention. A first image 381 is captured by actuating a first LED (or first group of LEDs) on one side of the camera's imaging stop. The actuated LED creates a first reflection artifact footprint 383 on the first image 381. A first image portion 385 excluding first footprint 383 is extracted from first image 381. First image portion 385 defines a first field-of-view FOV1. A second image 387 is captured by actuating a second LED (or second group of LEDs) physically displaced from the first LED. For example, the second LED (or second group of LEDs) may be positioned opposite to the first LED (or first group of LEDs) along the perimeter of the camera's imaging stop. Consequently, second image 387 has a second reflection artifact footprint 389 corresponding to the second LED (or to the second group of LEDs). A second image portion 386 excluding second footprint 389 is extracted from second image 387. Second image portion 386 defines a second field-of-view FOV2. First image portion 385 is then combined with second image portion 386, such as by montaging, to define a third image 391 having a third field-of-view FOV3 that spans both FOV1 and FOV2.

As is explained above, the present fundus imagers may be expanded to incorporate an iris camera. That is, an on-axis iris camera may be positioned behind the fundus camera 305 to aid in system alignment.

Figure 12:
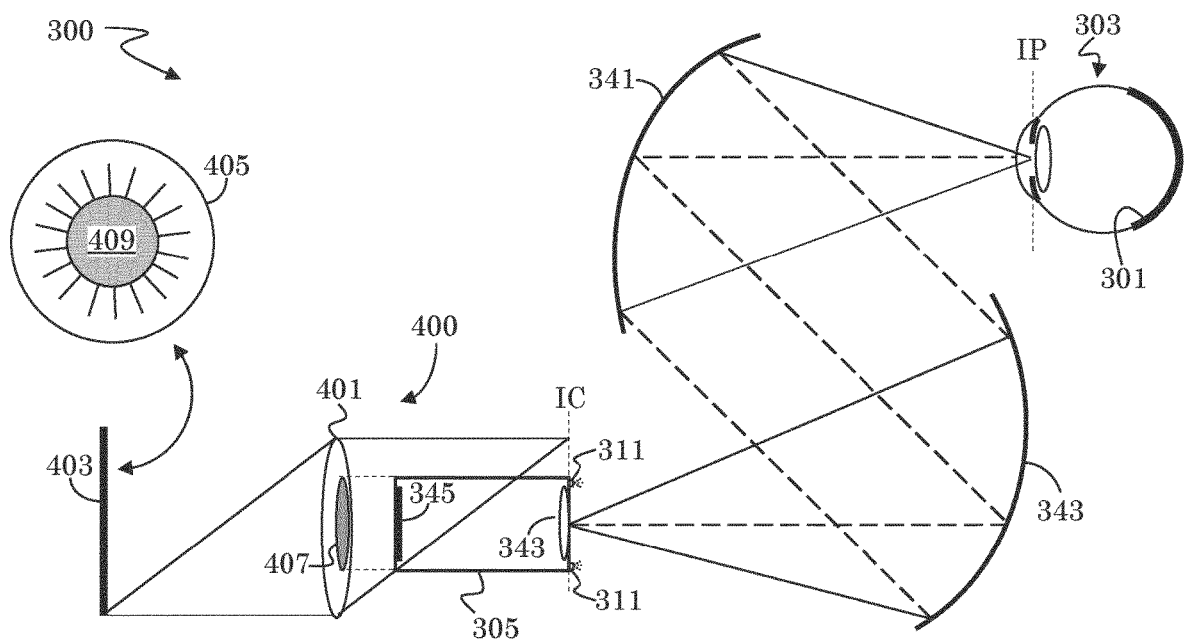
FIG. 12 illustrates the inclusion of a pupil (or iris) camera into the present fundus imager setup.

FIG. 12 illustrates the inclusion of an iris (or pupil) camera 400 into the present fundus imager setup. All elements similar to those of FIG. 6 have similar reference characters and are described above. As it would be understood, the pupil plane may be similar to the iris plane. Nonetheless for ease if discussion, the iris plane of eye 303 is labeled as IP, and its conjugate/image on camera 305 is labeled as iris conjugate IC. Lens 401 may be used in a 2f configuration to relay the iris image at iris conjugate plane IC onto an additional photosensor 403. An exemplary iris image 405, as may be captured by photosensor 403, is also shown. In this configuration, camera 305 casts a shadow 407 onto lens 401, which results in a shadow region 409 on iris image 405. When camera 305 is correctly aligned (e.g., centered at the eye iris), shadow region 409 would be at the center of iris image 405. A misalignment would cause shadow region 409 to be off-center in iris image 405. Thus, shadow region 409 may be used by a technician or the patient as an alignment indicator.

Figure 13:
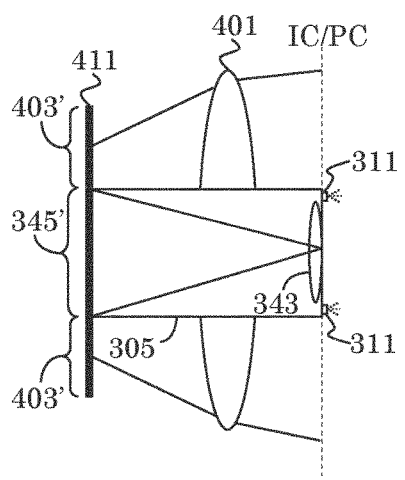
FIG. 13 illustrates a configuration wherein both the retina and iris are imaged onto the same photosensor in a fully integrated and miniaturized design.

FIG. 13 illustrates a configuration wherein both the retina and iris are imaged onto the same sensor 411 in a fully integrated and miniaturized design. All elements similar to those of FIGS. 6 and 12 have similar reference character and are described above. As explained above, the iris conjugate and pupil conjugate may be substantially similar (e.g., the same), and so this conjugate plane is labeled IR/PC in FIG. 13. In this compact configuration, lens 401 may have an annulus shape and surround camera 305. That is, lens 401 may be modified to have an aperture through which camera 305 may be inserted. Furthermore, sensors 345 and 403 are combined into a single sensor 411 having two imaging regions. A first central imaging region 345' is positioned to image the eye fundus from plane IC/PC through camera 305, and a second (perimeter) imaging region 403' surrounding the first imaging region 345' images the iris from plane IC/PC. That is, lens 401 focuses the iris from plane IP/IC onto second imaging region 403' in a manner similar to that of FIG. 12.

Figure 14:
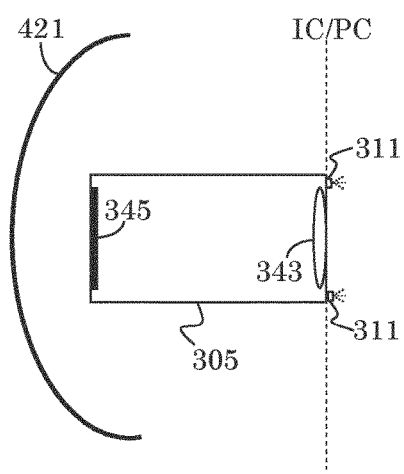
FIG. 14 illustrates a configuration to aid self-alignment of the fundus camera.

As stated above, the present configuration may be used by a patient for self-alignment of the fundus camera. FIG. 14 illustrates an alternate configuration to aid self-alignment of the fundus camera. In the present configuration, a curved reflective surface (e.g., mirror) 421 is place behind camera 305 and positioned to send an image of the iris similar to image 405 of FIG. 12 to the patient. That is, reflective surface 421 is on the optical axis of camera 305 to provide an image of the patient's iris back to the eye being imaged. For example, lens 401 of FIG. 12 may be replaced by reflective surface 421 to image the iris with a shadow region corresponding to the position of camera 305.

Figure 15:
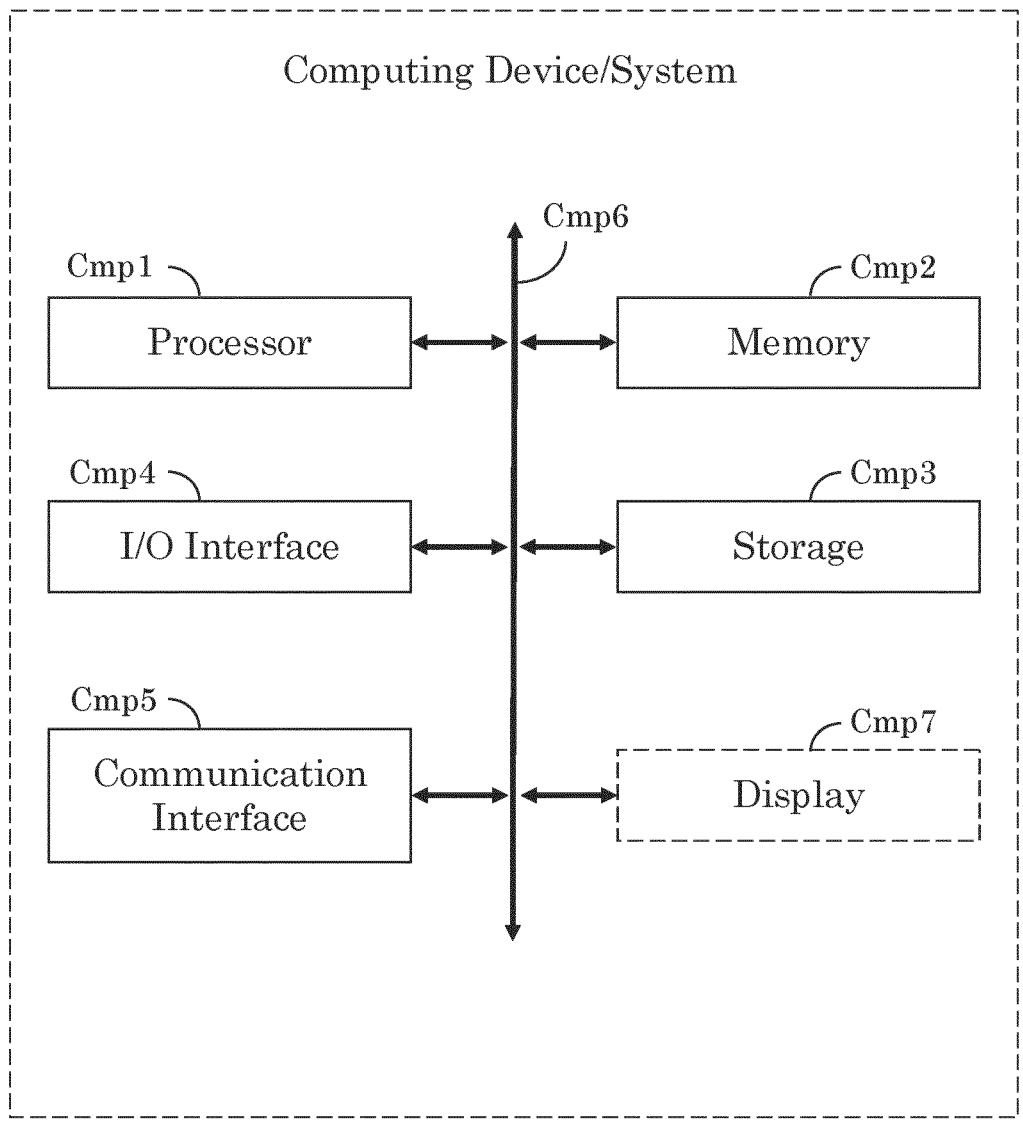
FIG. 15 illustrates an example computer system (or computing device or computer device).

FIG. 15 illustrates an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cmp1, memory Cmp2, storage Cmp3, an input/output (I/O) interface Cmp4, a communication interface Cmp5, and a bus Cmp6. The computer system may optionally also include a display Cmp7, such as a computer monitor or screen.

Processor Cmp1 includes hardware for executing instructions, such as those making up a computer program. For example, processor Cmp1 may be a central processing unit (CPU) or a general-purpose computing on graphics processing unit (GPGPU). Processor Cmp1 may retrieve (or fetch) the instructions from an internal register, an internal cache, memory Cmp2, or storage Cmp3, decode and execute the instructions, and write one or more results to an internal register, an internal cache, memory Cmp2, or storage Cmp3. In particular embodiments, processor Cmp1 may include one or more internal caches for data, instructions, or addresses. Processor Cmp1 may include one or more instruction caches, one or more data caches, such as to hold data tables. Instructions in the instruction caches may be copies of instructions in memory Cmp2 or storage Cmp3, and the instruction caches may speed up retrieval of those instructions by processor Cmp1. Processor Cmp1 may include any suitable number internal registers, and may include one or more arithmetic logic units (ALUs). Processor Cmp1 may be a multi-core processor; or include one or more processors Cmp1. Although this disclosure describes and illustrates a particular processor, this disclosure contemplates any suitable processor.

Memory Cmp2 may include main memory for storing instructions for processor Cmp1 to execute or to hold interim data during processing. For example, the computer system may load instructions or data (e.g., data tables) from storage Cmp3 or from another source (such as another computer system) to memory Cmp2. Processor Cmp1 may load the instructions and data from memory Cmp2 to one or more internal register or internal cache. To execute the instructions, processor Cmp1 may retrieve and decode the instructions from the internal register or internal cache. During or after execution of the instructions, processor Cmp1 may write one or more results (which may be intermediate or final results) to the internal register, internal cache, memory Cmp2 or storage Cmp3. Bus Cmp6 may include one or more memory buses (which may each include an address bus and a data bus) and may couple processor Cmp1 to memory Cmp2 and/or storage Cmp3. Optionally, one or more memory management unit (MMU) facilitate data transfers between processor Cmp1 and memory Cmp2. Memory Cmp2 (which may be fast, volatile memory) may include random access memory (RAM), such as dynamic RAM (DRAM) or static RAM (SRAM). Storage Cmp3 may include long-term or mass storage for data or instructions. Storage Cmp3 may be internal or external to computer system, and include one or more of a disk drive (e.g., hard disk drive, HDD, or solid-state drive, SSD), flash memory, ROM, EPROM, optical disc, a magneto-optical disc, magnetic tape, Universal Serial Bus (USB)-accessible drive, or other type of non-volatile memory.

I/O interface Cmp4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device or a combination of two or more of these.

Communication interface Cmp5 may provide network interfaces for communication with other systems or networks. Communication interface Cmp5 may include a Bluetooth interface or other type of packet-based communication. For example, communication interface Cmp5 may include a network interface controller (NIC) and/or a wireless NIC or a wireless adapter for communicating with a wireless network. Communication interface Cmp5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cmp6 may provide a communication link between the above mentioned components of the computing system. For example, bus Cmp6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. An ophthalmic diagnostic system for imaging an eye, comprising:
 a detector configured for capturing an image of the eye, the detector having a detector aperture;
 at least a first light source and a second light source proximate to the detector aperture; and
 one or more data processors;
 wherein:
 the detector configured to capture a first image of the eye with the first light source actuated and the second light source not actuated, and configured to capture a second image of the eye with the second light source actuated and the first light source not actuated and configured to generate output signals in response thereto; and
 the one or more data processors are configured to use the output signals to extract a first section of the first image excluding reflex artifacts from the first light source, extract a second section of the second image excluding reflex artifacts from the second light source, and combine the first and second sections to construct a composite image.

2. The ophthalmic diagnostic system of claim 1, further comprising at least a third light source, wherein:
the first light source and the second light source are configured to illuminate the retina of the eye and the third light source is configured to illuminate the pupil of the eye; and
the detector has a first imaging region conjugate to the retina of the eye and a second imaging region conjugate to the pupil of the eye.

3. The ophthalmic diagnostic system of claim 2, wherein the third light source is an infrared light source and the first light source and the second light source are visible light sources.

4. The ophthalmic diagnostic system of claim 2, wherein the detector includes a first photo-detector array in front of a second photo-detector array along an axial optical path of the detector, the first imaging region being within the first photo-detector array, and the second imaging region being within the second photo-detector array.

5. The ophthalmic diagnostic system of claim 4, further comprising:
a detector lens having an outer region surrounding a central aperture along the axial optical path of the detector, the diameter of the aperture being large enough to prevent the detector lens from receiving reflected light from the retina of the eye, the outer region configured to focus reflected light from the pupil of the eye to the second imaging region of the second photo-detector array.

6. The ophthalmic diagnostic system of claim 5, wherein:
the first photo-detector array is part of a first camera unit;
the second photo-detector array is part of a second camera unit; and
the first camera unit is inserted within the central aperture.

7. The ophthalmic diagnostic system of claim 2, wherein the first imaging region and second imaging region are defined within a single photo-detector array.

8. The ophthalmic diagnostic system of claim 1, further comprising a curved reflector surrounding the detector and directed towards the eye, the reflector configured to provide an image of the eye viewable by the patient, wherein the image of the eye viewable by the patient is indicative of an alignment of the detector with the eye.

9. The ophthalmic diagnostic system of claim 1, further comprising a first curved reflector separated from a second curved reflector in an optic path from the detector aperture and to the eye, with no system lens within the optic path.

10. The ophthalmic diagnostic system of claim 9, wherein:
the first curved reflector configured to receive light from the first light source and the second light source are configured to at a first field-of-view (FOV), and configured to reflect the received light to the second curved reflector; and
the second curved reflector configured to reflect the received light from the first reflector to the eye at a second FOV different than the first FOV.

11. The ophthalmic diagnostic system of claim 10, wherein the second FOV is greater than the first FOV.

12. The ophthalmic diagnostic system of claim 9, wherein the separation between the first curved reflector and the second curved reflector is configured to be adjusted to compensate for a refractive error in the eye.

13. The ophthalmic diagnostic system of claim 1, wherein:
the captured first image includes the upper hemisphere and lower hemisphere of the eye; and
the captured second image includes the upper hemisphere and lower hemisphere of the eye.

14. The ophthalmic diagnostic system of claim 1, wherein:
the extracted first section includes the entirety of an upper hemisphere or a lower hemisphere of the imaged eye; and
the extracted second section includes the entirety of the other of the upper hemisphere or the lower hemisphere of the imaged eye.

15. The ophthalmic diagnostic system of claim 1, wherein the excluded reflex artifacts from the first light source and the second light source includes corneal reflex and lacks system lens artifacts.

16. The ophthalmic diagnostic system of claim 1, wherein:
the first light source and the second light source are adjacent to the detector aperture; and
the first light source, the second light source, and the detector share the same optics for illumination and detection.

17. An ophthalmic diagnostic system for imaging an eye of a patient, comprising:
a detector configured for capturing an image of the eye, the detector having a detector aperture;
at least one light source proximate to the detector aperture; and
a curved reflector at least partially surrounding the detector and directed towards the eye, the reflector configured to provide an image of the eye viewable by the patient;
wherein the image of the eye viewable by the patient is indicative of an alignment of the detector to the eye, and is configured to be usable by the patient to self-align the detector to the eye's iris.

18. The ophthalmic diagnostic system of claim 17, wherein:
the curved reflector is behind the detector and on an optical axis of the detector; and
the image of the eye viewable by the patient includes an image of the eye's pupil with a shadow region corresponding to a position of the detector, and the detector is configured to be aligned to the eye's iris by aligning the shadow region to a central region of the image of the eye's pupil.

19. The ophthalmic diagnostic system of claim 17, further comprising:
a user-input configured to control movement of the detector within at least one plane of motion;
wherein the user uses the user-input to self-align the detector to the iris.

20. The ophthalmic diagnostic system of claim 17, further comprising at least one second curved reflector in an optic path between the detector aperture and the eye, with no system lens within the optic path.

21. The ophthalmic diagnostic system of claim 17, wherein the least one light source includes at least one infrared light source and one visible light source.

* * * * *